(12) United States Patent
Takeda et al.

(10) Patent No.: US 7,558,609 B2
(45) Date of Patent: Jul. 7, 2009

(54) CEREBRAL-ISCHEMIA SUPERVISORY MONITOR

(75) Inventors: Yoshimasa Takeda, Okayama (JP); Kiyoshi Morita, Okayama (JP)

(73) Assignee: National University Corporation Okayama University, Okayama (JP)

( * ) Notice: Subject to any disclaimer, the term of this patent is extended or adjusted under 35 U.S.C. 154(b) by 323 days.

(21) Appl. No.: 11/547,731

(22) PCT Filed: Mar. 3, 2005

(86) PCT No.: PCT/JP2005/003634

§ 371 (c)(1), (2), (4) Date: Oct. 6, 2006

(87) PCT Pub. No.: WO2005/099585

PCT Pub. Date: Oct. 27, 2005

(65) Prior Publication Data

US 2007/0215824 A1    Sep. 20, 2007

(30) Foreign Application Priority Data

Apr. 6, 2004    (JP) ............................. 2004-112315

(51) Int. Cl.
*A61B 5/145* (2006.01)
(52) U.S. Cl. .................... 600/310; 600/317; 600/407
(58) Field of Classification Search .............. 600/310, 600/317, 322, 323, 340, 473, 476
See application file for complete search history.

(56) References Cited

U.S. PATENT DOCUMENTS

| | | | | | |
|---|---|---|---|---|---|
| 4,945,896 | A | * | 8/1990 | Gade | 600/202 |
| 5,916,171 | A | * | 6/1999 | Mayevsky | 600/476 |
| 7,130,672 | B2 | * | 10/2006 | Pewzner et al. | 600/324 |

(Continued)

FOREIGN PATENT DOCUMENTS

CN    1068952    2/1993

(Continued)

OTHER PUBLICATIONS

Eliyahu Pevzner, Assaf Deutsch, Tamar Manor, Nava Dekel, Revital Etziony, Igor Derzy, Nisim Razon and Avraham Mayevsky: "Real-time Multiparametric Spectroscopy as a Practical Tool for Evaluation of Tissue Vitality In Vivo" Proceedings of the SPIE, vol. 4958, 2003, pp. 171-182, XP 00218163 (12 pages).

(Continued)

*Primary Examiner*—Eric F Winakur
*Assistant Examiner*—Etsub D Berhanu
(74) *Attorney, Agent, or Firm*—Osha • Liang LLP

(57) ABSTRACT

A cerebral-ischemia supervisory monitor includes: a pair of optical fibers which each have a tip part that can be placed substantially perpendicularly to an exterior surface of a cerebrum; an irradiation portion which is connected to a basic end part of one of the optical fibers, and via this optical fiber, can irradiate the exterior surface of a cerebrum with ultraviolet rays; a light-receiving portion which is connected to the basic end part of the other one of the optical fibers, and via this optical fiber, can receive fluorescence that is emitted when the ultraviolet rays excite cerebral cells; and a display portion which can display an intensity of the fluorescence.

7 Claims, 10 Drawing Sheets

U.S. PATENT DOCUMENTS

2002/0062061 A1 5/2002 Kaneko et al.
2004/0209237 A1* 10/2004 Flewelling et al. ............. 435/4

FOREIGN PATENT DOCUMENTS

| JP | 10-508763 | 9/1998 |
| JP | 2001-509589 | 7/2001 |
| JP | 2004-504092 | 2/2004 |
| WO | 92/12705 A1 | 8/1992 |
| WO | 95/32664 | 12/1995 |
| WO | WO-95/32664 | 12/1995 |
| WO | WO-99/02956 | 1/1999 |
| WO | WO-02/07592 | 1/2002 |

OTHER PUBLICATIONS

Avraham Mayevsky, Tamar Manor, Eliyahu Pevzner, Assaf Deutsch, Revital Etziony, Nava Dekel.: "Real-time Optical Monitoring of Tissue Vitality In vivo" Proceedings of the SPIE, vol. 4616, 2002, pp. 30-39, XP002518164 (10 pages).

* cited by examiner

CEREBRAL-ISCHEMIA SUPERVISORY MONITOR

TECHNICAL FIELD

The present invention relates to an apparatus which is capable of deciding whether the quantity of oxygen which is supplied to a cerebrum is proper or not.

BACKGROUND ART

In general, as a treatment for a cerebral aneurysm, a clipping operation is performed as shown in FIG. 11. In this clipping operation, upstream from an aneurysm 100, a clip 101 is attached to a cerebral artery 102 so that the flow of blood can once be stopped in the cerebral artery 102. In this state, a clip 103 is attached to the root of the aneurysm 100. This prevents blood from flowing into the aneurysm 100, thereby evading a rupture of the aneurysm 100.

After this process has been completed, the clip 101 is detached so that the flow of blood can be recovered in the cerebral artery 102. Then, the incised head part of a patient is closed with the clip 103 remaining inside of the cerebrum.

However, in such a clipping operation, the flow of blood in the cerebral artery 102 stops temporarily, even though it is merely a short period of time. Hence, during this period, the oxygen which is supplied to the cerebrum is running short. This shortage of oxygen may kill cerebral cells. In other words, it is known that it may cause so-called ischemic neuronal damage.

This has raised a demand for an apparatus which is capable of monitoring the balance of oxygen supply and oxygen demand in a cerebrum during the clipping operation, so that such ischemic neuronal damage can be kept under control.

In view of the above described disadvantages, it is an object of the present invention to provide a cerebral-ischemia supervisory monitor which is capable of monitoring the balance of oxygen supply and oxygen demand in a cerebrum during the clipping operation, and deciding whether it is proper or not.

DISCLOSURE OF THE INVENTION

In order to resolve those disadvantages, a cerebral-ischemia supervisory monitor according to the present invention, comprising: a pair of optical fibers which each have a tip part that is placed toward the exterior surface of a cerebrum; an irradiation portion which is connected to the basic end part of one of the optical fibers, and via this optical fiber, irradiates the exterior surface of a cerebrum with ultraviolet rays; a light-receiving portion which is connected to the basic end part of the other one of the optical fibers, and via this optical fiber, receives fluorescence that is emitted when the ultraviolet rays excite cerebral cells; a control portion which controls the irradiation and irradiation stop of ultraviolet rays by the irradiation portion, and calculates the intensity of the fluorescence received by the light-receiving portion; and a display portion which displays the intensity of the fluorescence calculated by the control portion.

According to the present invention, the ultraviolet rays which are applied to the exterior surface of a cerebrum excite cerebral cells, and then, the intensity of the emitted fluorescence is calculated. Herein, the reason that "the ultraviolet rays excite cerebral cells" is because the oxygen which is supplied to the cerebrum is running short, thus, NADH (or (reduced) nicotinamide adenine dinucleotide) increases in the mitochondria of the cerebral cells, and this NADH is excited by the ultraviolet rays to emit blue fluorescence.

Therefore, according to the present invention, the intensity of fluorescence which increases when the supplied oxygen is running short can be displayed. Thus, a comparison is made, for example, between a reference fluorescence intensity which is preset as data at the time when oxygen is in short supply and the displayed fluorescence intensity. This makes it possible for medical workers to decide whether or not the quantity of oxygen which is supplied to a cerebrum is proper.

Herein, the above described display portion displays fluorescence intensity, using numerical values. However, how to display it is not limited to this. For example, it also includes a graphic display, using a plotter.

BEST MODE FOR CARRYING OUT THE INVENTION

Hereinafter, a preferred embodiment of the present invention will be described with reference to the drawings.

Figure 1:
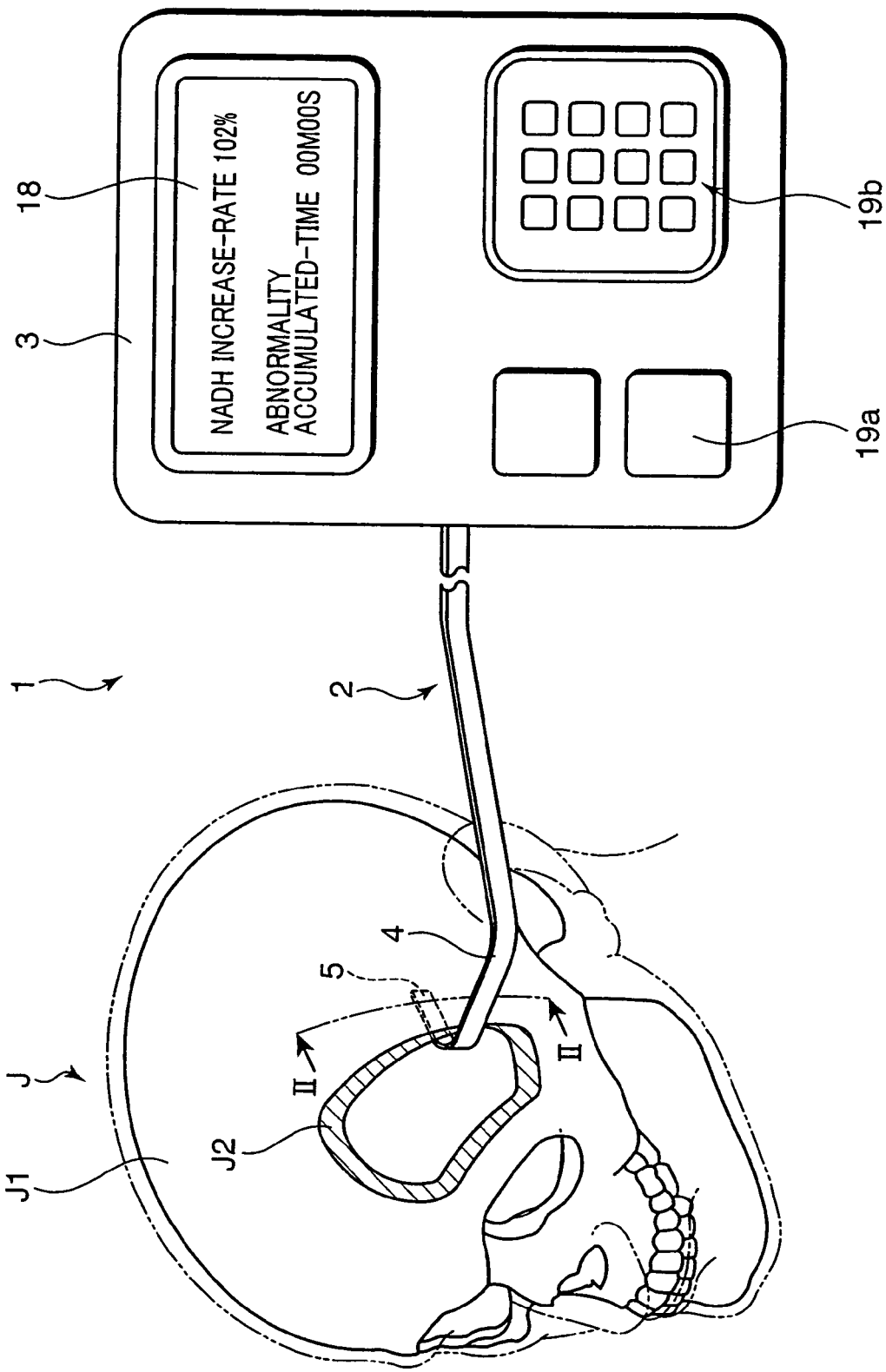
FIG. 1 is a schematic view of the whole configuration of a cerebral-ischemia supervisory monitor according to the embodiment of the present invention.
Figure 2A:
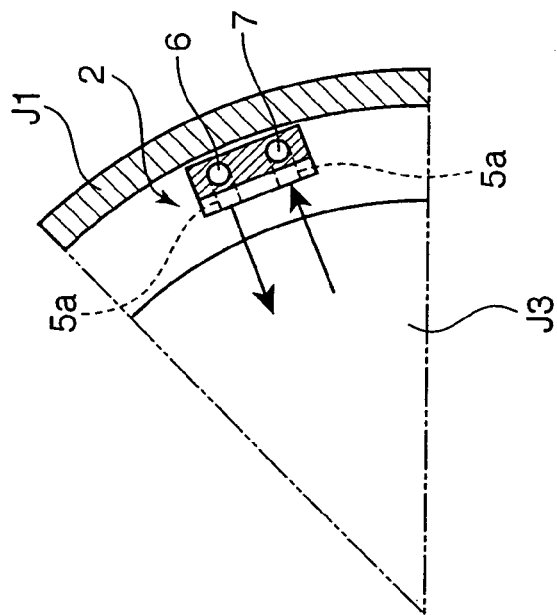
FIG. 2A is a sectional view, seen along a II-II line in FIG. 1.
Figure 2B:
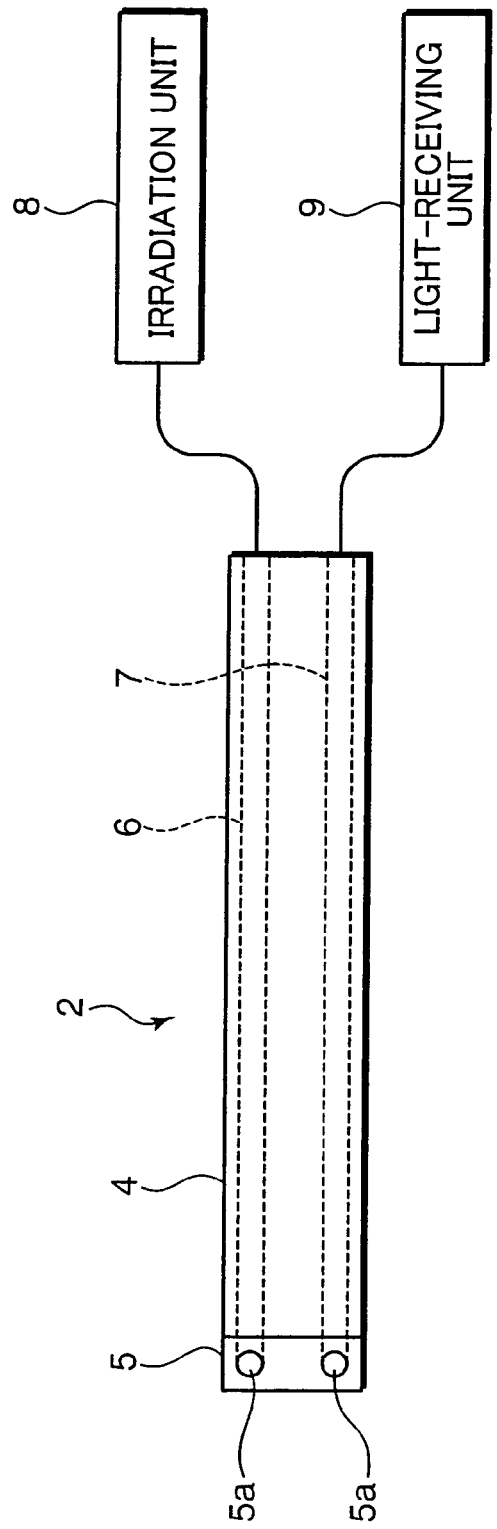
FIG. 2B is an enlarged plan view of a cable belt in FIG. 1.

FIG. 1 is a schematic view of the whole configuration of a cerebral-ischemia supervisory monitor 1 according to the embodiment of the present invention, showing a state where it is used for a clipping operation for a cerebral aneurysm. FIG. 2A is a sectional view, seen along a II-II line in FIG. 1. FIG. 2B is an enlarged plan view of a cable belt 2 in FIG. 1.

With reference to each figure, the cerebral-ischemia supervisory monitor 1 includes: the cable belt 2 having a tip part which can be inserted into cranial bones J1 of a patient J that are kept incised for the clipping operation; and a supervisory apparatus body 3 which is connected to the basic end part of this cable belt 2.

The cable belt 2 is a belt-shaped member as a whole. It is made of a material which can undergo plastic deformation, such as aluminum and a film of fluororesin or the like thereon. This cable belt 2 includes: a main portion 4 which passes through an incised head part J2 that is formed in the cranial bones J1 and searches along the interior surface of the cranial bones J1; and a bent-tip portion 5 which is bent substantially perpendicularly in the thickness directions of the main portion 4.

The cable belt 2 has a pair of optical fibers 6, 7 built-in, in parallel in its width directions and along its length directions. The tip part of each optical fiber 6, 7 is bent along the bent-tip portion 5. It is kept open outside of the cable belt 2 through an opening 5a which is formed in the end surface of the bent-tip portion 5. Therefore, if the main portion 4 searches along the interior surface of the cranial bones J1, the tip part of each optical fiber 6, 7 can be placed in substantially perpendicular directions to the cranial bones J1, or as shown in FIG. 2A, substantially perpendicularly to the circumferential surface of a cerebrum J3.

In the optical fiber 6, an irradiation unit 8 is connected to its basic end part. The ultraviolet rays which are applied by this irradiation unit 8 is led to its tip part. On the other hand, to the basic end part of the optical fiber 7, a light-receiving unit 9 is connected, and the light which is taken in from its tip part is guided to the light-receiving unit 9.

As shown in FIG. 2A, with the cable belt 2 kept inserted between the cranial bones J1 and the cerebrum J3, each optical fiber 6, 7 is positioned in the cable belt 2. Thereby, if ultraviolet rays are applied to the exterior surface of the cerebrum J3 through the optical fiber 6, the ultraviolet rays excite cerebral cells and thus fluorescence is emitted. Then, the emitted fluorescence and the light which has been reflected from the exterior surface of the cerebrum J3 can be led to the light-receiving unit 9 through the optical fiber 7.

Figure 3:
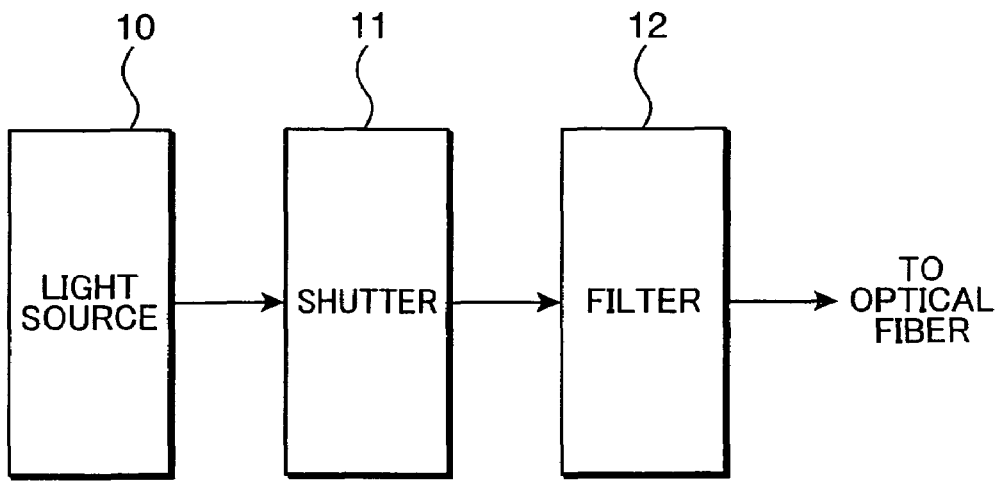
FIG. 3 is a schematic block diagram, showing the configuration of an irradiation unit shown in FIG. 2.
Figure 4:
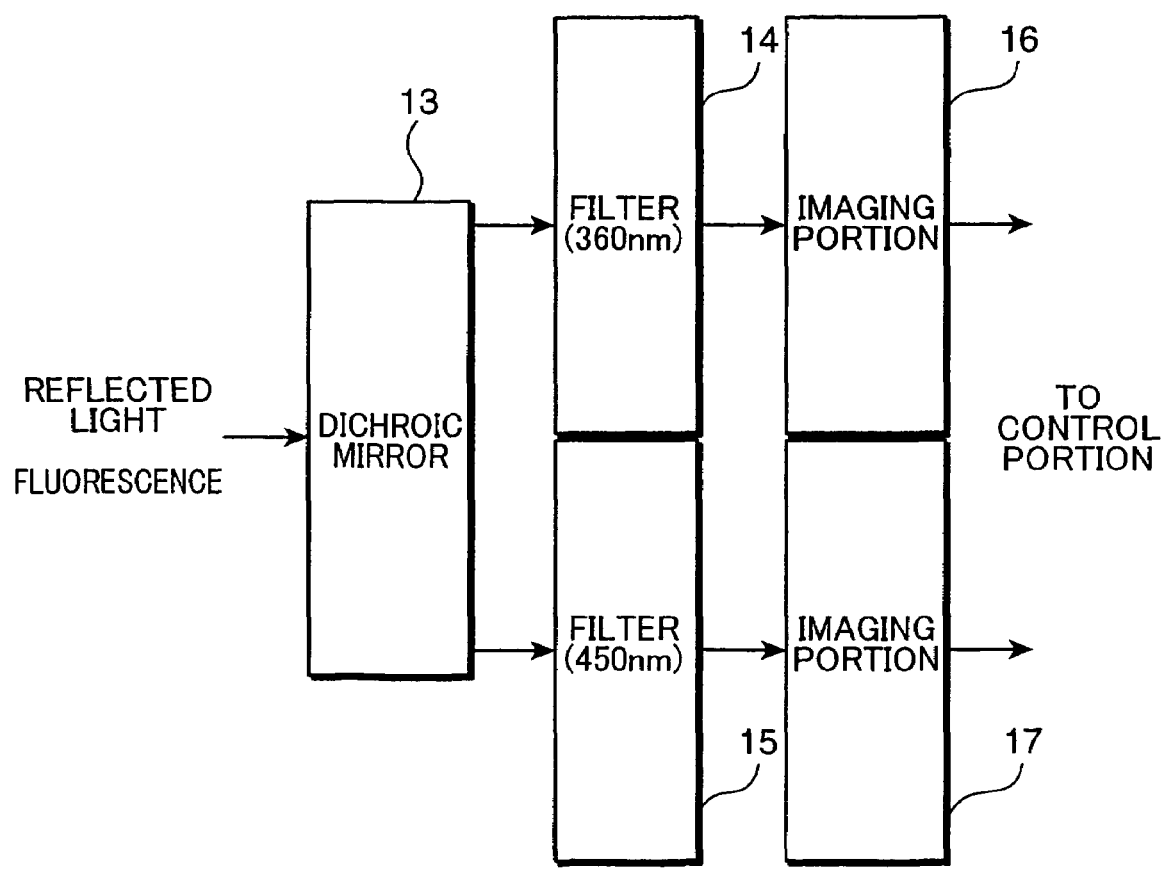
FIG. 4 is a schematic block diagram, showing the configuration of a light-receiving unit shown in FIG. 2.

FIG. 3 and FIG. 4 are schematic block diagrams, showing the configuration of the irradiation unit 8 and the light-receiving unit 9 shown in FIG. 2.

With reference to FIG. 3, the irradiation unit 8 includes: a light source 10 which can apply ultraviolet rays; a shutter 11 which can open and close an optical path of this light source 10; and a filter 12 which extracts the light having a desired wavelength from among the ultraviolet rays that have passed through this shutter 11. This light that has passed through the filter 12 is guided to the basic end part of the optical fiber 6.

Herein, the light source 10 is publicly known, which includes: a xenon lamp, a mercury lamp or the like which has a power of about 200 watts; and a reflector which reflects the ultraviolet rays that have been applied from this lamp. The irradiation intensity of ultraviolet rays by the light source 10 is designed so that the irradiation intensity of ultraviolet rays which are applied from the tip part of the optical fiber 6 becomes 0.3 mW/cm$^2$.

The shutter 11 is placed between the light source 10 and the filter 12. The timing in which it is opened and closed is controlled by a control portion 20 (which will be described later). From among the ultraviolet rays which have been applied from the light source 10, the light that has a wavelength of 360 nm passes through the filter 12.

With reference to FIG. 4, the light-receiving unit 9 includes: a dichroic mirror 13 which allows the light that is taken into the optical fiber 7 to branch into two systems of visible rays and ultraviolet rays; a filter 14 which extracts, from among those ultraviolet rays, light that has a wavelength of 360 nm; a filter 15 which extracts, from among the visible rays, light that has a wavelength of 450 nm; and imaging portions (e.g., a CCD, a cooling CCD and a CMOS sensor) 16, 17 which image the light that has been extracted by each filter 14, 15, respectively. The image data obtained when each imaging portion 16, 17 has imaged it is inputted in the control portion 20 (described later).

Again, with reference to FIG. 1, the supervisory apparatus body 3 includes: a display 18 which is made up of an LCD (or liquid crystal display) and the like; an input portion 19 which has a start key 19a, a ten key 19b, or the like; and the control portion 20 which is connected to these display 18 and input portion 19.

Figure 5:
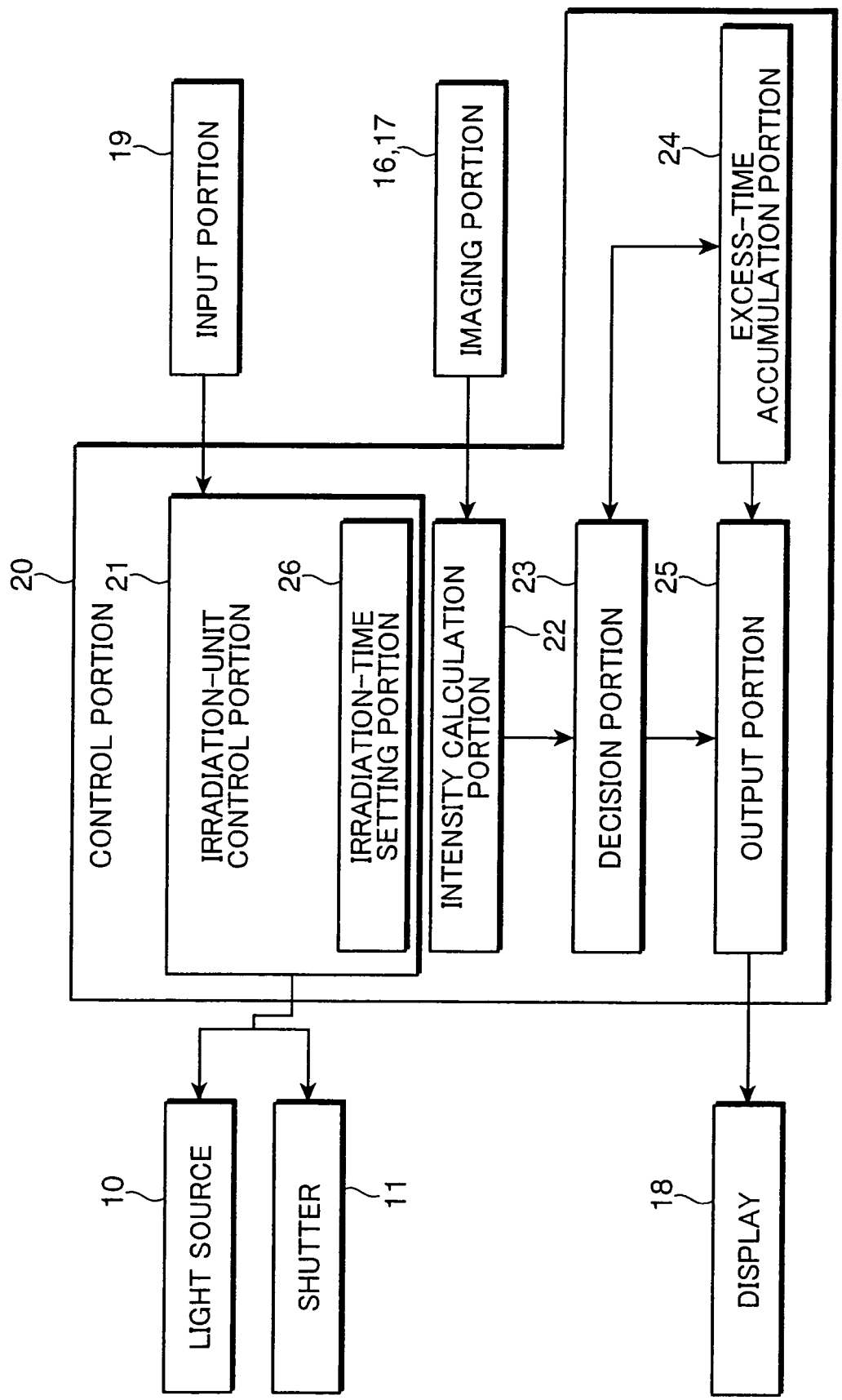
FIG. 5 is a schematic block diagram, showing the configuration of a control portion which is incorporated into an ischemia examination monitor of FIG. 1.

FIG. 5 is a schematic block diagram, showing the configuration of the control portion 20 which is incorporated into an ischemia examination monitor 1 of FIG. 1.

With reference to FIG. 5, the control portion 20 is publicly known, and includes as its basic configuration: a CPU which executes various arithmetic processing; an ROM which stores an initialization or the like; and an RAM which stores set information or the like that is inputted, so that its overwriting can be executed.

This control portion 20 functions mainly as: an irradiation-unit control portion 21 which controls the drive of the irradiation unit 8, based on information which is inputted by the input portion 19; an intensity calculation portion 22 which calculates the intensity of the light that has been received, using the image data which is inputted from each imaging portion 16, 17; a decision portion 23 which decides whether the quantity of oxygen which is supplied to a cerebrum is proper or not, based on the intensity of the light calculated by this intensity calculation portion 22; an excess-time accumulation portion 24 which accumulates a period of time in a state where the decision has been made by this decision portion 23 that oxygen is in short supply; and an output portion 25 which allows the display 18 to display the decision result by the decision portion 23 and the accumulated time by the excess-time accumulation portion 24.

When the above described start key 19a is pushed, the irradiation-unit control portion 21 opens the shutter 11, and thus, ultraviolet rays by the light source 10 are applied to the side of the optical fiber 6. Specifically, the irradiation-unit control portion 21 includes an irradiation-time setting portion 26 which can set a period of time when the shutter 11 is opened and closed, according to the input of a numerical value by the above described ten key 19b.

Figure 6:
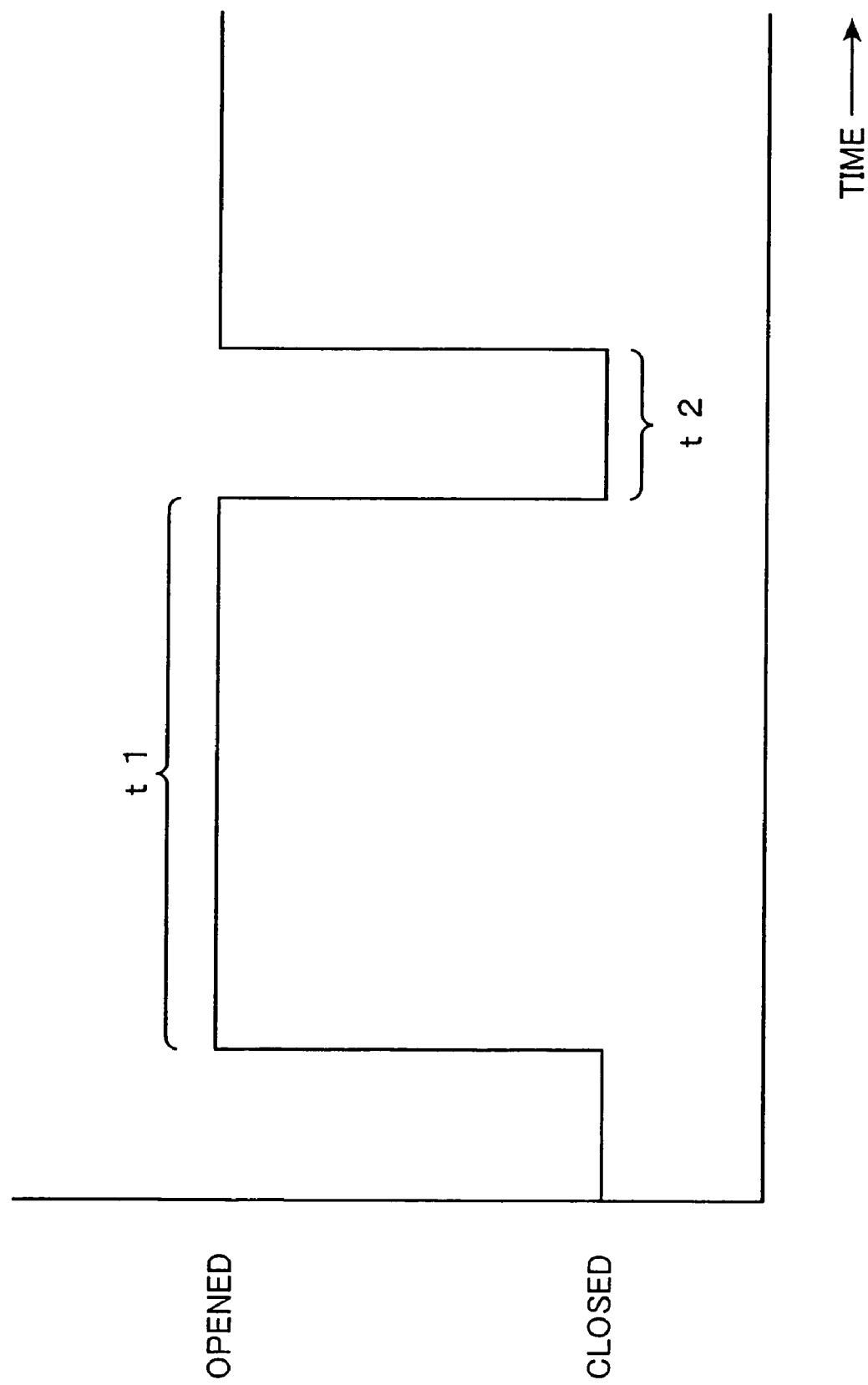
FIG. 6 is a timing chart, showing the opening and closing control of a shutter by the control portion.

As shown in FIG. 6, the irradiation-time setting portion 26 stores the shutter 11's opening time t1 and closing time t2 which have been inputted by the ten key 19b. According to both times t1, t2, the shutter 11 is opened and closed. Herein, the irradiation-time setting portion 26 inhibits the opening time t1 from being set to two seconds or shorter. This will later be described in detail.

According to this embodiment, the intensity calculation portion 22 calculates the intensity (i.e., electric charge) of light inside of the image data which has been accumulated within the opening time t1.

The decision portion 23 decides whether or not the ratio of a fluorescence intensity K1 which has been calculated this time to a fluorescence intensity K (refer to FIG. 7) at the time when the flow of blood in the cerebral artery is stopped, or K1/K×100, is 120 percent or higher. If it is 120 percent, then it directs the excess-time accumulation portion 24 to accumulate a period of time. In addition, it decides whether or not the time accumulated by the excess-time accumulation portion 24 is beyond 18 minutes. If it is beyond 18 minutes, then it decides that the oxygen which is supplied to the cerebrum is running short to the extent that may cause hypoxic damage to the cerebrum.

Figure 7:
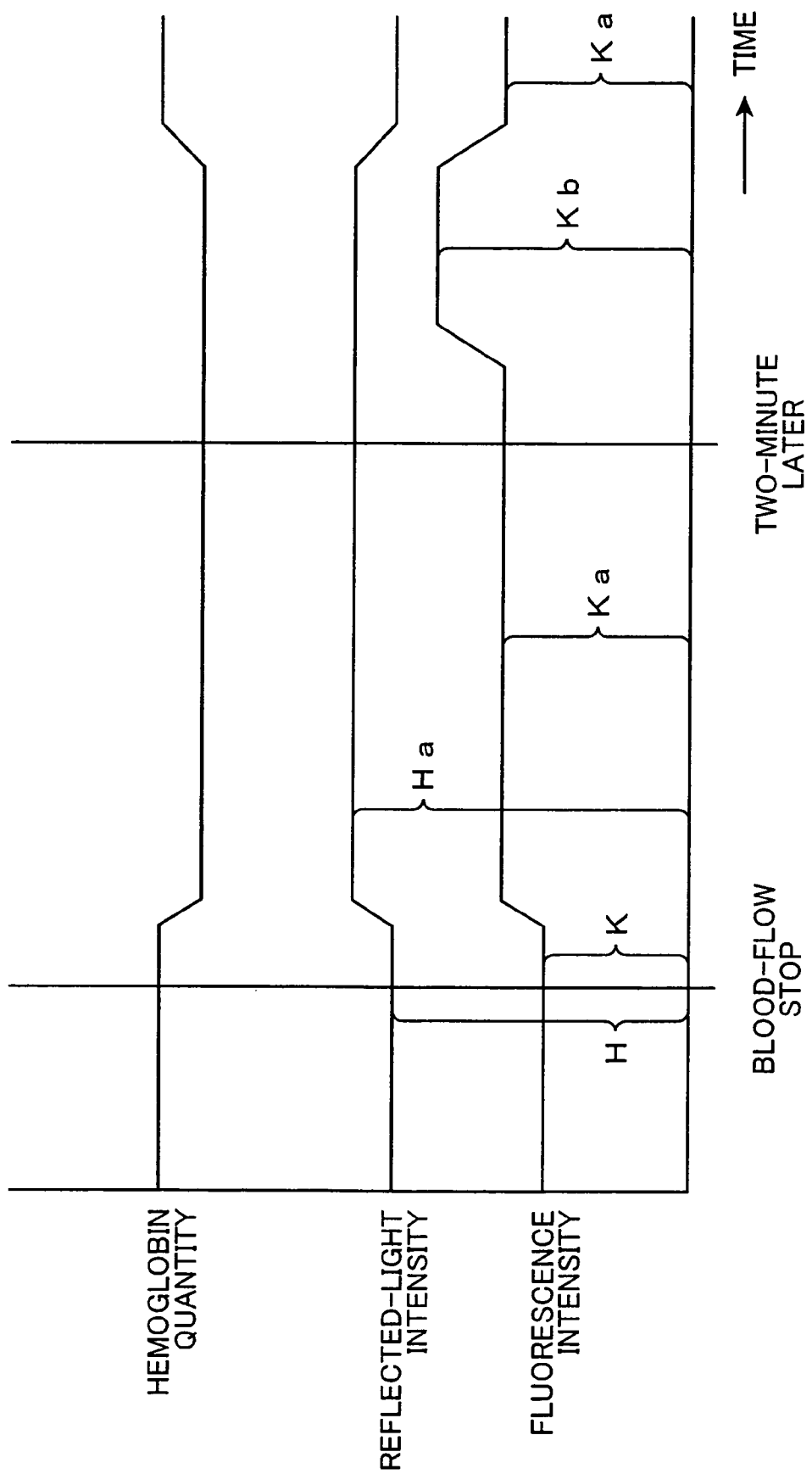
FIG. 7 is a graphical representation, showing fluctuations in the quantity of hemoglobin, the intensity of reflected light and the intensity of fluorescence.

As shown in FIG. 7, a reflected-light intensity H increases slightly for a while after the flow of blood in the cerebral artery has been stopped, and it becomes an intensity Ha. This is attributed to a reduction in the quantity of hemoglobin after the flow of blood in the cerebral artery has been stopped. Hence, as the quantity of hemoglobin decreases, the fluorescence intensity from cerebral cells increases.

In other words, the fluorescence intensity which is calculated for a while after the flow of blood has been stopped can include the rise in the fluorescence intensity which is attributed to a reduction in the quantity of hemoglobin. Therefore, if the reflected-light intensity is on the increase, then the decision portion 23 stops the excess-time accumulation portion 24 from accumulating a period of time. On the other hand, if the reflected-light intensity is kept stable (i.e., at the reflected-light intensity Ha) after its increase, then according to a rise in the fluorescence intensity, it allows the excess-time accumulation portion 24 to accumulating a period of time.

On the other hand, the fluorescence intensity K increases when the quantity of hemoglobin decreases, and it becomes an intensity Ka. Then, after the quantity of hemoglobin has become stable (i.e., after approximately two minutes have passed since the flow of blood in the cerebral artery was stopped), it rises further to an intensity Kb. However, if the flow of blood in the cerebral artery is returned, this reduces it again to the intensity Ka, or below Ka. Then, the decision portion 23 decides whether or not the calculated fluorescence intensity has decreased below the intensity Ka after it once rose to the intensity Kb. If it has decreased, then it judges that the flow of blood in the cerebral artery has returned, and finishes measuring the reflected-light intensity and fluorescence.

If the flow of blood in the cerebral artery is returned, the quantity of hemoglobin and the reflected-light intensity are also returned to substantially the same state as before the flow of blood was stopped (i.e., the quantity of hemoglobin increases and the reflected-light intensity drops).

Hereinafter, processing which is executed by the control portion 20 will be described with reference to FIG. 8.

Figure 8:
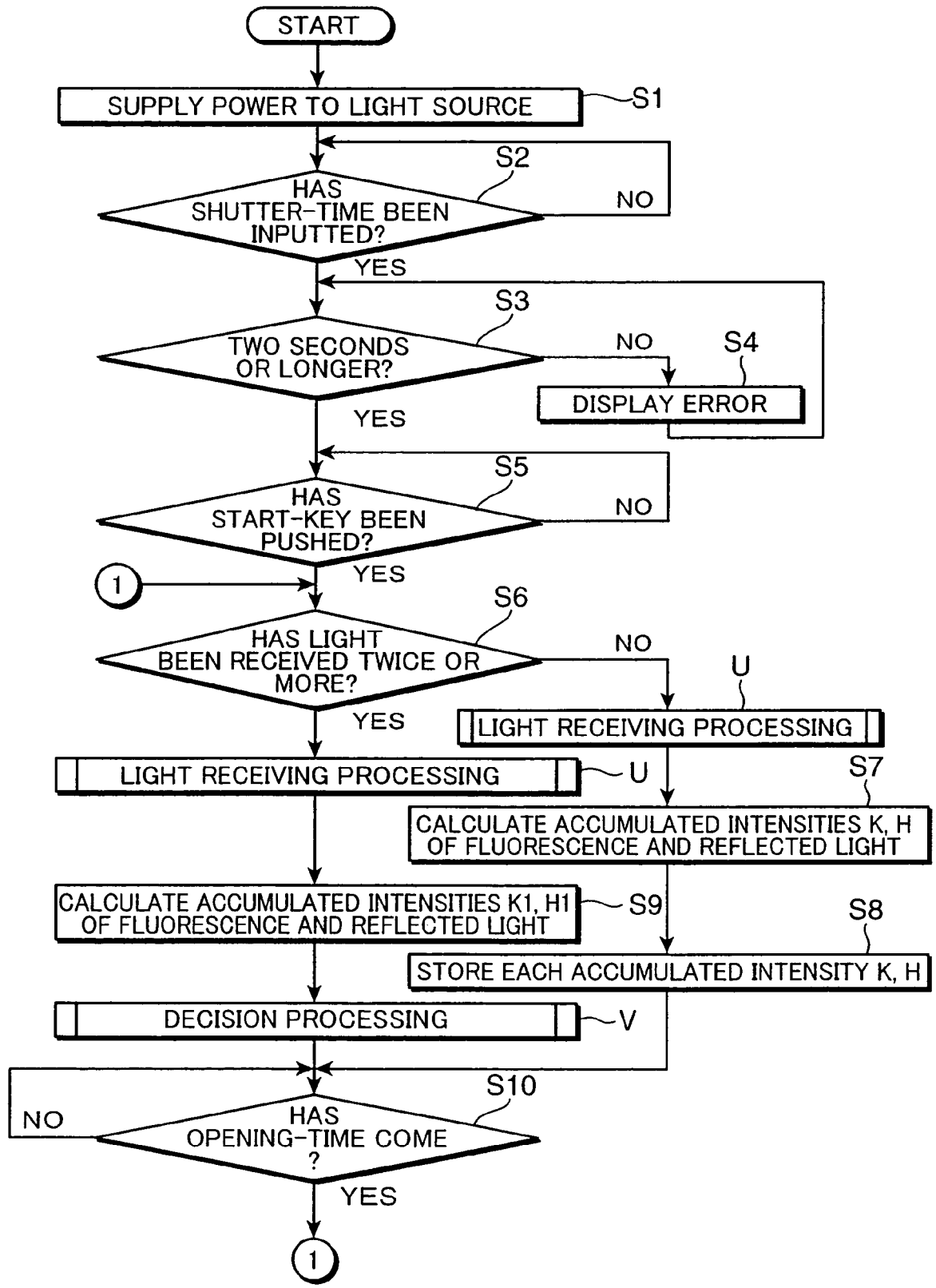
FIG. 8 is a flow chart, showing processing which is executed by the control portion of FIG. 5.

FIG. 8 is a flow chart, showing processing which is executed by the control portion 20 of FIG. 5.

First, a medical worker turns on a power switch (not shown). If the power switch is turned on, the control portion 20 supplies electric power to the light source 10 (in a step S1). Then, the light source 10 is initialized (which takes about fifteen minutes, depending upon the type of the light source 10).

Next, as shown in FIG. 1, the medical worker sets up the ischemia supervisory monitor 1, before giving a treatment for stopping the flow of blood in the cerebral artery (i.e., in timing when the worker is about to halt the flow of blood).

Then, the control portion 20 decides whether or not the shutter's opening time t1 and closing time t2 have been inputted by the ten key 19b (in a step S2).

If the decision is made that both times t1, t2 have not yet been inputted (i.e., NO at the step S2), the step S2 is repeated. On the other hand, if the decision is made that both times t1, t2 have been inputted (i.e., YES at the step S2), a decision is made whether or not the inputted opening time t1 is two seconds or longer (in a step S3). Herein, if the decision is made that it is shorter than two seconds (i.e., NO at the step S3), then an error is displayed on the display 18 (in a step S4) and the step S3 is repeated.

On the other hand, if the decision is made that it is two seconds or longer (i.e., YES at the step S3), a decision is made whether or not the start key 19a has been pushed (in a step S5). Herein, if the decision is made that the start key 19a has not been pushed (i.e., NO at the step S5), the step S5 is repeated. On the other hand, if the decision is made that the start key 19a has been pushed (i.e., YES at the step S5), a decision is made whether or not the light receiving to be executed from now is the second one or after it (in a step S6).

Herein, a medical worker pushes the start key 19a, and thereafter, gives a treatment for stopping the flow of blood in a cerebral artery (such as attaching a clip to the cerebral artery).

Then, if the decision is made that the light receiving is the first one (i.e., NO at the step S6), then light-receiving processing U is executed.

Figure 9:
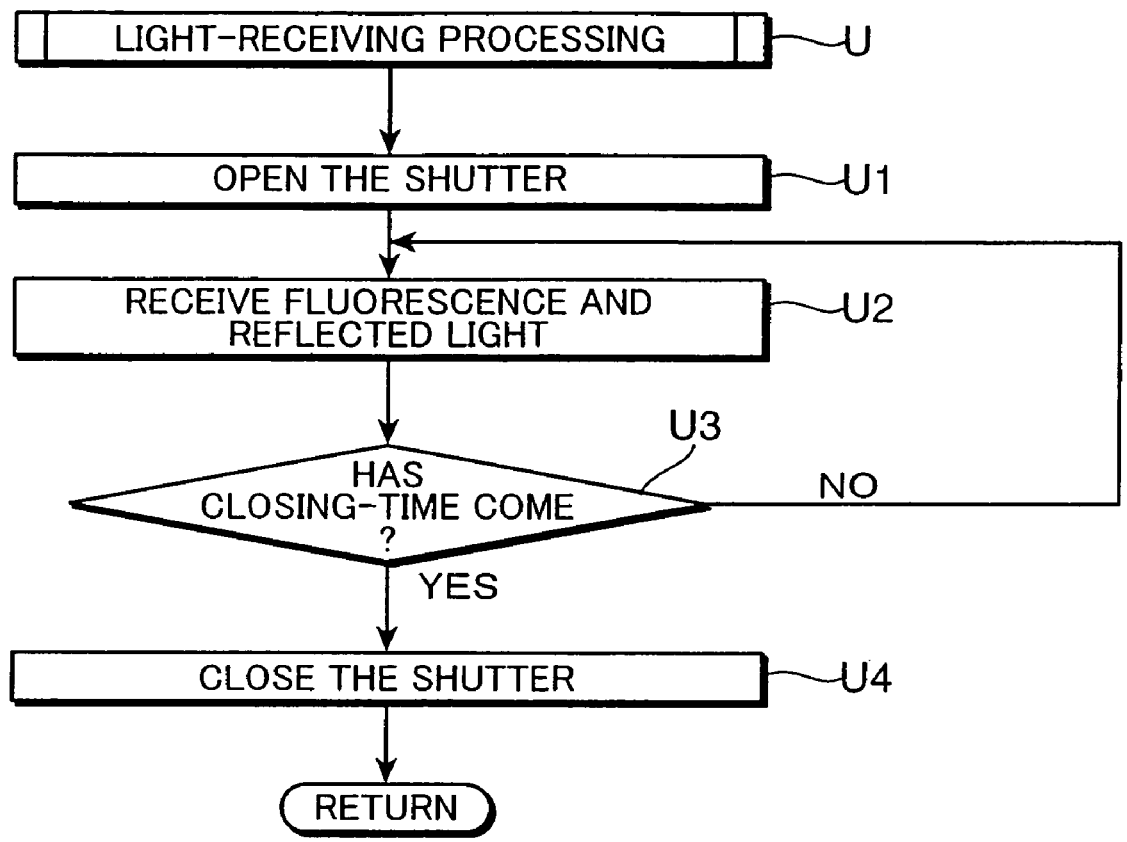
FIG. 9 is a flow chart, showing light-receiving processing in FIG. 8.

FIG. 9 is a flow chart, showing light-receiving processing in FIG. 8.

With reference to FIG. 9, if the light-receiving processing U is started, first, the shutter 11 is opened (in a step U1). Next, the ultraviolet rays which have been applied excite cerebral cells. Then, the fluorescence which have been emitted and the reflected light of the ultraviolet rays from the cerebrum J3 are separately received (in a step U2).

Next, a decision is made whether or not it is time to start the closing time t2 of the shutter 11 (i.e., whether or not the opening time t1 has been completed) (in a step U3). Herein, if the decision is made that the opening time t1 has not yet been completed (i.e., NO at the step U3), the step U2 is repeated.

On the other hand, if the decision is made that it is time to start the closing time t2 of the shutter 11 (i.e., YES at the step U3), the shutter 11 is closed (in a step U4) and the processing is returned to the main routine of FIG. 8.

Again, with reference to FIG. 8, next, the intensities K, H (refer to FIG. 7) of the received fluorescence and reflected light are calculated (in a step S7). Then, each intensity K, H is stored (in a step S8), and a decision is made whether or not the time to start the opening time t1 has come (i.e., whether or not the closing time t2 has been completed) (in a step S10).

Herein, if the decision is made that the closing time t2 has not yet been completed (i.e., NO at the step S10), the step S10 is repeated. On the other hand, if the decision is made that the time to start the opening time t1 has come (i.e., YES at the step S10), the above described step S6 is executed.

On the other hand, if the decision is made that the light receiving is the second one or after it (i.e., YES at the step S6), then the above described light-receiving processing U is executed. In this light-receiving processing U, the intensities K1, H1 (refer to FIG. 7) of the received fluorescence and reflected light are calculated (in a step S9). Next, decision processing V is executed. Herein, reference characters and numerals K1, H1 are given for the purpose of distinguishing them from the intensities K, H which were calculated at the first time (i.e., in timing when the flow of blood came close to a halt). The intensities which are received at the second time or after are all denoted by K1, H1.

Figure 10:
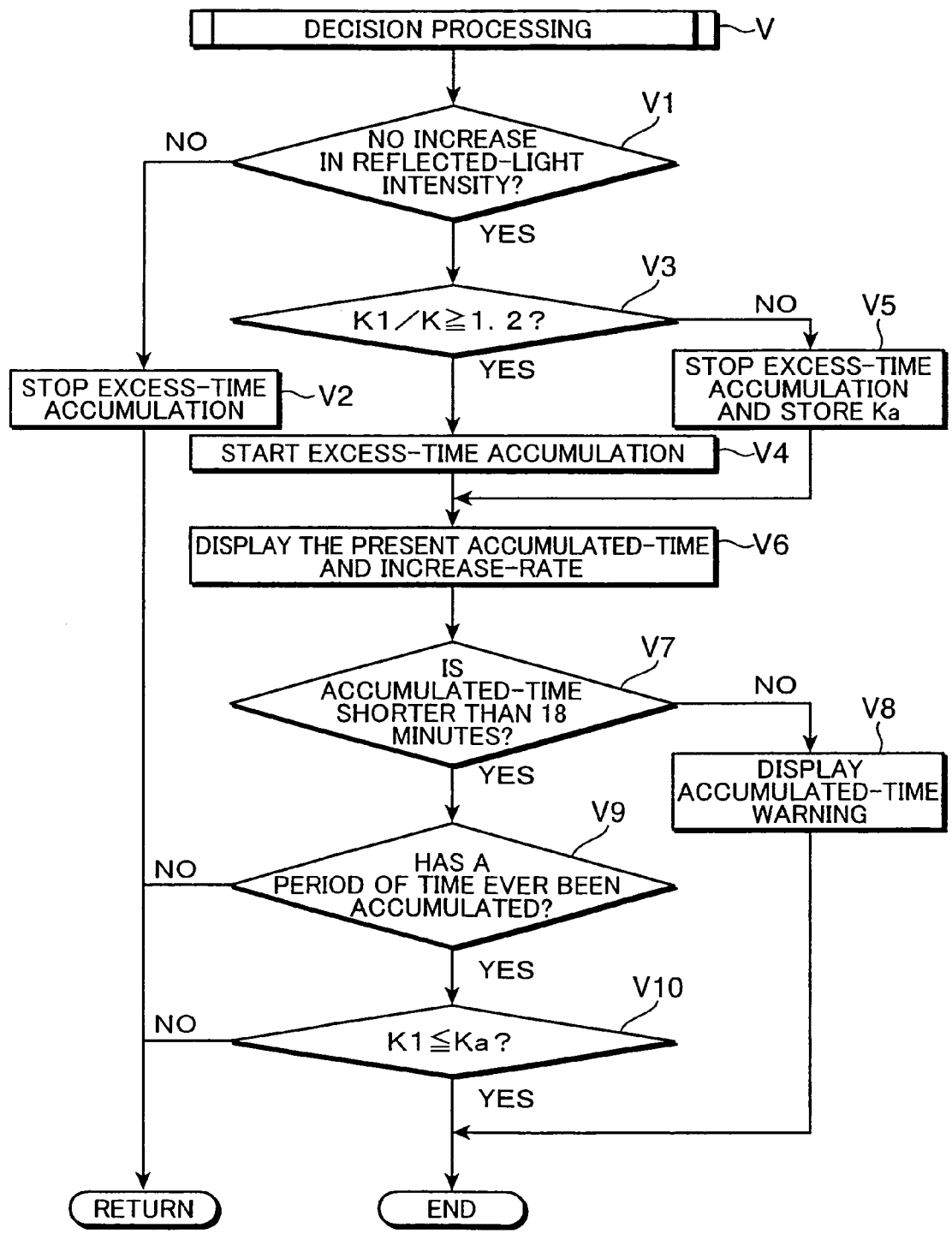
FIG. 10 is a flow chart, showing decision processing in FIG. 8.
Figure 11:
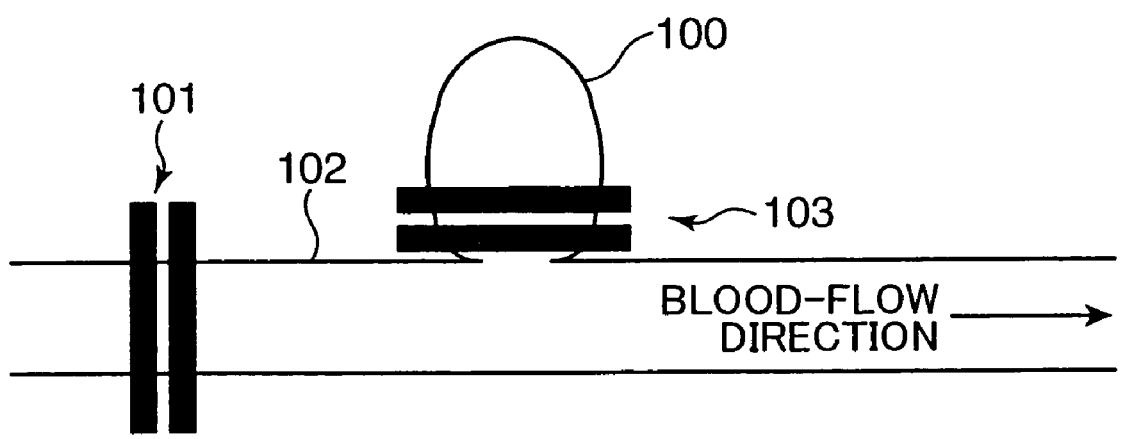
FIG. 11 is a schematic illustration, showing how to perform a clipping operation.

FIG. 10 is a flow chart, showing the decision processing V in FIG. 8.

With reference to FIG. 10, if the decision processing V is executed, first, with respect to two reflected-light intensities which have been continually calculated, a comparison is made between the reflected-light intensities which have been calculated this time and the last time (e.g., if the light receiving this time is the second one, the intensities H, H1 are compared). Then, a decision is made whether the intensity which has been calculated this time is not greater than the intensity which was calculated the preceding time (in a step V1).

Herein, if the decision is made that the intensity of reflected light has increased (i.e., unsatisfied with at the step V1), then in the case where a step V4 (described later) was executed before (i.e., when an excess period of time is being accumulated), the accumulation is stopped (in a step V2). Then, a return is made to the main routine in FIG. 8.

On the other hand, if the decision is made that the intensity of reflected light has not increased (i.e., satisfied with at the step V1), the rate of increase from the intensity K at the first time to the intensity K1 this time is calculated. Then, a decision is made whether or not it is 120 percent or higher (in a step V3). If the decision is made that it is 120 percent or higher (i.e., YES at the step V3), then a period of time starts to be accumulated (in the step V4). On the other hand, if the decision is made that it is lower than 120 percent (i.e., YES at the step V3), then in the case where the step V4 was executed before, the accumulation is stopped (in a step V5).

Herein, at the time when the step V5 is executed, the intensity of reflected light is not on the rise (i.e., satisfied with at the step V1), and at the same time, the rate of an increase in the intensity of fluorescence is lower than 20 percent (i.e., NO at the step V3). In other words, the calculated fluorescence intensity K1 is equivalent to Ka of FIG. 7. Therefore, in the step V5, in addition to the above described processing, the fluorescence intensity K1 calculated this time is stored as Ka. Herein, when the intensity Ka is stored, the intensity K1 of this time is compared with the intensity K1 of the last time. If these intensities K1, K1 are substantially equal to each other (i.e., as shown in FIG. 7, if the intensity of fluorescence is substantially constant), it is preferable that this intensity K1 be stored as Ka.

After the step V4 or the step V5 has been executed, the accumulated time and the rate of an increase in the intensity of fluorescence at present are displayed on the display 18 (in a step V6: refer to FIG. 1). Then, a decision is made whether or not the accumulated time is shorter than 18 minutes (in a step V7).

If the decision is made that the accumulated time is 18 minutes or longer (i.e., NO at the step V7), the fact that the accumulated time is beyond a given value is displayed on the display 18 (in a step V8). Then, the processing is terminated.

Herein, in the above described decision processing V, after the fact that the accumulated time is beyond a given value is displayed (in the step V8), the processing is supposed to be terminated. However, the process is not limited to this. For example, following the step V8, a return may also be made to the step S10 of the main routine in FIG. 8.

On the other hand, if the decision is made that the accumulated time is shorter than 18 minutes (i.e., YES at the step V7), then a decision is made whether or not a period of time has been accumulated after the start of the processing (i.e., after the push of the start key 19a) before the present time. In other words, a decision is made whether or not the intensity of fluorescence K1 has increased up to the intensity equivalent to Kb of FIG. 7 (in the step V9).

If the decision is made that a period of time has not been accumulated (i.e., NO at the step V9), the step S10 of the main routine in FIG. 8 is executed. On the other hand, if the decision is made that a period of time has been accumulated (i.e., YES at the step V9), then a decision is made whether or not the intensity K1 which has been calculated this time is equal to, or lower than, Ka (refer to FIG. 7) which has been stored at the above described step V5 (in the step V10).

If the decision is made that K1 is equal to, or greater than, Ka (i.e., NO at the step V10), the step S10 of the main routine in FIG. 8 is executed. On the other hand, if the decision is made that K1 is equal to, or lower than, Ka (i.e., YES at the step V10), then the judgment is made that the flow of blood in the cerebral artery has returned, and the processing is terminated.

As described hereinbefore, according to the ischemia supervisory monitor 1, the intensity of fluorescence which increases at the time when oxygen is in short supply can be displayed. Thus, a comparison is made, for example, between a reference fluorescence intensity which is preset as data at the time when oxygen is in short supply and the displayed fluorescence intensity. This makes it possible for medical workers to decide whether or not the quantity of oxygen which is supplied to a cerebrum is proper.

According to the configuration where each optical fiber 6, 7 is placed inside of the cable belt 2, the plasticity of the cable belt 2 allows the shape of each optical fiber 6, 7 to be relatively freely changed. In addition, in the case where the main portion 4 searches along the cranial bones J1, using the bent-tip portion 5, each optical fiber 6, 7 can be directed to the side of the exterior surface of the cerebrum J3.

According to the configuration where the accumulated intensity of fluorescence is calculated within the time t1 when the shutter 11 is opened for two seconds or longer, the intensity of fluorescence which is accumulated during one heartbeat of a patient can be calculated. This makes it possible to calculate the fluorescence intensity more steadily.

According to the configuration where the rate of change in fluorescence intensity is displayed on the display 18 from the fluorescence intensity which is first calculated after the control portion 20 has started to execute control to the fluorescence intensity which is secondly and later calculated, with respect to a patient, the relative rate of an increase in the quantity of NADH can be displayed. This provides medical workers with information which excludes the factor of errors that can be caused by the difference between individuals, such as a patient's physical constitution.

Furthermore, according to the ischemia supervisory monitor 1, if the fluorescence-intensity change rate becomes higher than 20 percent and the accumulated period of time in that state is beyond 18 minutes, the decision can be made that the oxygen which is supplied to a cerebrum is running short to the extent that may cause hypoxic damage to the cerebrum. Herein, these rates of change and accumulated period of time are not limited to 20 percent and 18 minutes, respectively. They can be adjusted within the range where the oxygen which is supplied to the cerebrum is prevented from running short. Specifically, they can be adjusted to smaller values than those set values.

According to the configuration where a period of time is not accumulated if the intensity of the reflected light of ultraviolet rays increases, the decision can be more precisely made that the oxygen which is supplied to the cerebrum is running short.

Herein, in the step V1 (refer to FIG. 10) according to this embodiment, if the reflected-light intensity which is calculated this time is greater than the reflected-light intensity which was calculated the preceding time, the accumulation of a period of time comes to a halt. However, the process is not limited to this. For example, if the reflected-light intensity is increasing at a predetermined rate (e.g., 5 percent) or higher, the accumulation of a period of time can also be stopped.

Furthermore, according to this embodiment, the rate of an increase in the intensity of fluorescence and the accumulated period of time are displayed. However, the process is not limited to this. For example, as shown in FIG. 7, each parameter can also be graphically displayed. Moreover, the display portion is not limited to the display 18 such as an LCD. It can also be configured by a plotter or the like which can print the above described graph.

As described in the above, a cerebral-ischemia supervisory monitor according to the present invention comprising: a pair of optical fibers which each have a tip part that is placed toward the exterior surface of a cerebrum; an irradiation portion which is connected to the basic end part of one of the optical fibers, and via this optical fiber, irradiates the exterior surface of a cerebrum with ultraviolet rays; a light-receiving portion which is connected to the basic end part of the other one of the optical fibers, and via this optical fiber, receives fluorescence that is emitted when the ultraviolet rays excite cerebral cells; a control portion which controls the irradiation and irradiation stop of ultraviolet rays by the irradiation portion, and calculates the intensity of the fluorescence received by the light-receiving portion; and a display portion which displays the intensity of the fluorescence calculated by the control portion.

According to the above configuration, the ultraviolet rays which are applied to the exterior surface of a cerebrum excite cerebral cells, and then, the intensity of the emitted fluorescence is calculated. Herein, the reason that "the ultraviolet rays excite cerebral cells" is because the oxygen which is supplied to the cerebrum is running short, thus, NADH (or (reduced) nicotinamide adenine dinucleotide) increases in the mitochondria of the cerebral cells, and this NADH is excited by the ultraviolet rays to emit blue fluorescence.

Therefore, according to the above configuration, the intensity of fluorescence which increases when the supplied oxygen is running short can be displayed. Thus, a comparison is made, for example, between a reference fluorescence intensity which is preset as data at the time when oxygen is in short supply and the displayed fluorescence intensity. This makes it possible for medical workers to decide whether or not the quantity of oxygen which is supplied to a cerebrum is proper.

Herein, the above described display portion displays fluorescence intensity, using numerical values. However, how to display it is not limited to this. For example, it also includes a graphic display, using a plotter.

In the above described cerebral-ischemia supervisory monitor, preferably, each optical fiber is disposed inside of a belt-shaped member which undergoes plastic deformation, in parallel in the width directions thereof and along the length directions thereof; the belt-shaped member includes a main portion which passes through an opening portion that is formed in cranial bones and searches along the interior surface of the cranial bones, and a bent-tip portion which is bent substantially perpendicularly in the thickness directions of the main portion.

According to the configuration where each optical fiber is placed inside of the belt-shaped member, the plasticity of the belt-shaped member allows the shape of each optical fiber to be relatively freely changed. In addition, in the case where the main portion searches along the cranial bones, using the bent-tip portion, the tip of each optical fiber can be directed substantially perpendicularly to the exterior surface of the cerebrum.

In the above described cerebral-ischemia supervisory monitor, preferably, the irradiation portion includes a light source, and a shutter which is disposed between the light source and the optical fiber and opens and closes an optical path of the light source; and the control portion controls the timing in which the shutter is opened and closed, keeps the shutter open for two seconds or longer when it is opened, and calculates the fluorescence intensity that is accumulated during this opening period of time.

According to the configuration where the accumulated intensity of fluorescence is calculated within the time when the shutter is opened for two seconds or longer, the intensity of fluorescence which is accumulated during one heartbeat (shorter than two seconds) of a patient can be calculated. This makes it possible to calculate the fluorescence intensity more steadily.

In other words, the volume of the cerebrum changes due to the fluctuation of cerebral blood volume which is generated by the heart beat. The distance varies between the tip of an optical fiber in place and the exterior surface of the cerebrum. Then, this variation in the distance can vary the received fluorescence intensity. However, as described above, if the time when the shutter is kept open is two seconds or longer, the fluorescence intensity can be calculated as data including the fluorescence intensity in both states where the cerebrum contracts and relaxes. This prevents instantaneous fluctuations in the received fluorescence intensity from being added.

In the above described cerebral-ischemia supervisory monitor, preferably, based on the fluorescence intensity which is first calculated after it starts to execute control and the fluorescence intensity which is secondly and later calculated, the control portion calculates the rate of change in fluorescence intensity, and allows the display portion to display this rate of change.

According to the configuration where the rate of change in fluorescence intensity is displayed from the fluorescence intensity which is first calculated after control has been started to the fluorescence intensity which is secondly and later calculated, the first calculation is made in timing when the flow of blood in the cerebral artery comes close to a halt. Therefore, with respect to a patient, the relative rate of an increase in the quantity of NADH can be displayed. This provides medical workers with information which excludes the factor of errors that can be caused by the difference between individuals, such as a patient's physical constitution.

In the above described cerebral-ischemia supervisory monitor, preferably, if the fluorescence-intensity change rate is a predetermined value or higher, the control portion decides that the oxygen which is supplied to a cerebrum is running short.

At this time, if the fluorescence-intensity change rate becomes a predetermined value or higher, the decision is made that the oxygen which is supplied to the cerebrum is running short. This allows the apparatus itself to decide that the oxygen which is supplied to the cerebrum is running short.

In the above described cerebral-ischemia supervisory monitor, preferably, the control portion accumulates periods of time when the fluorescence-intensity change rate is a predetermined value or higher, and if this accumulated period is a predetermined period or longer, decides that the oxygen which is supplied to a cerebrum is running short to the extent that may cause hypoxic damage to the cerebrum.

With this configuration, the periods of time when the fluorescence intensity is a predetermined value or higher are accumulated, and this accumulated period is made a parameter. This prevents the cerebrum from having hypoxic damage.

In the above described cerebral-ischemia supervisory monitor, preferably, the predetermined value of the fluorescence-intensity change rate is 20 percent, and the predetermined period of the accumulated period is 18 minutes.

Specifically, if the rate of change becomes higher than 20 percent and the accumulated period is beyond 18 minutes, it is known that the rate at which cerebral hypoxic damage (i.e., ischemic neuronal damage) is caused becomes higher. Hence, it is preferable that using these values, a decision be made whether the quantity of oxygen which is supplied to the cerebrum is proper or not.

In the above described cerebral-ischemia supervisory monitor, preferably, the light-receiving portion separately receives the ultraviolet rays which are reflected from a cerebrum and the fluorescence which is emitted according to the ultraviolet rays; and with respect to two reflected-light intensities which are continually calculated, if the reflected-light intensity which is calculated this time is greater than the reflected-light intensity which was calculated the preceding time, then the control portion does not accumulate this period of time, even though the fluorescence-intensity change rate of the fluorescence intensity which is calculated this time is the predetermined value or higher.

According to the configuration where a period of time is not accumulated if the intensity of the reflected light of ultraviolet rays increases, the decision can be more precisely made that the oxygen which is supplied to the cerebrum is running short.

In other words, if the flow of blood in a cerebral artery is stopped, the flow of blood in the cerebrum also comes to a halt. However, the flow of blood (i.e., venous blood flow) from the cerebrum to the whole body is not hindered. Thus, shortly after the flow of blood has been stopped in the cerebral artery, the blood inside of cerebral blood vessels decreases, thereby reducing hemoglobin in the blood of the cerebrum.

Herein, hemoglobin has a relatively-wide absorption wavelength range. Therefore, if its quantity decreases in the cerebrum, the quantity of ultraviolet rays which can be absorbed is also reduced. As a result, among the ultraviolet rays which have been applied, the light increases which is reflected from the exterior surface of the cerebrum. In addition, if the quantity of hemoglobin decreases in the cerebrum, the intensity of the fluorescence which is emitted by NADH also increases, because the quantity of the fluorescence which is absorbed by hemoglobin is reduced.

Then, if the flow of blood is kept stopped for a predetermined period of time (e.g., about two minutes), cerebral cells will fall into a hypoxia. Consequently, the quantity of the NADH which is inside of them increases, thus rapidly increasing the fluorescence intensity. At this time, the intensity of the reflected light remains unchanged.

Accordingly, for a while after the flow of blood has been stopped in the cerebral artery, the quantity of hemoglobin decreases, and thereby, the reflected light of the ultraviolet rays and the intensity of the fluorescence increase. In other words, for some time after the flow of blood has been stopped, the fluorescence intensity increases regardless of an increase in the quantity of NADH. Besides, it is known that the quantity of NADH increases after the intensity of the reflected light is increased as described above and then is stabilized. Hence, as described above, if a period of time is not accumulated while the intensity of the reflected light is increasing, then the decision can be prevented from being made that an increase in the intensity of fluorescence which is caused by a reduction in the quantity of hemoglobin is an increase in the quantity of NADH.

INDUSTRIAL APPLICABILITY

According to the present invention, ultraviolet rays which are applied to an exterior surface of a cerebrum excite cerebrum cells, and then, the intensity of an emitted fluorescence is calculated. Therefore, the intensity of fluorescence can be displayed. Thus, a comparison is made, for example, between a reference fluorescence intensity which is present as data at the time when oxygen is in short supply and the displayed fluorescence intensity. This makes it possible for medical workers to decide whether or not the quantity of oxygen which is supplied to a cerebrum is proper.

What is claimed is:

1. A cerebral-ischemia supervisory monitor, comprising:
a pair of optical fibers which each have a tip part that is capable of being placed toward an exterior surface of a cerebrum;
an irradiation portion which is connected to a basic end part of one of the optical fibers, and via this optical fiber, irradiates the exterior surface of a cerebrum with ultraviolet rays;
a light-receiving portion which is connected to the basic end part of the other one of the optical fibers, and via this optical fiber, receives fluorescence that is emitted when ultraviolet rays excite cerebral cells;
a control portion which controls the irradiation and irradiation stop of ultraviolet rays by the irradiation portion, and calculates an intensity of the fluorescence received by the light-receiving portion; and
a display portion which displays the intensity of the fluorescence calculated by the control portion, wherein:
each optical fiber is disposed inside of a belt-shaped member which undergoes plastic deformation, in parallel in a width direction thereof and along a length direction thereof; and
the belt-shaped member includes a main portion for passing through an opening portion that is formed in cranial bones and searches along an interior surface of the cranial bones, and a bent-tip portion which is bent substantially perpendicularly in a thickness direction of the main portion.

2. A cerebral-ischemia supervisory monitor, comprising:
a pair of optical fibers which each have a tip part that is capable of being placed toward an exterior surface of a cerebrum;
an irradiation portion which is connected to a basic end part of one of the optical fibers, and via this optical fiber, irradiates the exterior surface of a cerebrum with ultraviolet rays;
a light-receiving portion which is connected to the basic end part of the other one of the optical fibers, and via this optical fiber, receives fluorescence that is emitted when ultraviolet rays excite cerebral cells;
a control portion which controls the irradiation and irradiation stop of ultraviolet rays by the irradiation portion, and calculates an intensity of the fluorescence received by the light-receiving portion; and
a display portion which displays the intensity of the fluorescence calculated by the control portion, wherein:
the irradiation portion includes a light source, and a shutter which is disposed between the light source and the optical fiber and opens and closes an optical path of the light source; and
the control portion is configured to control the timing in which the shutter is opened and closed, keep the shutter open for two seconds or longer when it is opened, and calculate the fluorescence intensity that is accumulated during this opening period of time.

3. The cerebral-ischemia supervisory monitor according to claim 2, wherein based on the fluorescence intensity which is first calculated after it starts to execute control and the fluorescence intensity which is secondly and later calculated, the control portion is configured to calculate the rate of change in fluorescence intensity, and allow the display portion to display this rate of change.

4. The cerebral-ischemia supervisory monitor according to claim 3, wherein if the fluorescence-intensity change rate is a predetermined value or higher, the control portion is configured to decide that the oxygen which is supplied to a cerebrum is running short.

5. The cerebral-ischemia supervisory monitor according to claim 4, wherein the control portion is configured to accumulate periods of time when the fluorescence-intensity change rate is a predetermined value or higher, and if this accumulated period is a predetermined period or longer, decide that the oxygen which is supplied to a cerebrum is running short to the extent that may cause hypoxic damage to the cerebrum.

6. The cerebral-ischemia supervisory monitor according to claim 5, wherein the predetermined value of the fluorescence-intensity change rate is 20 percent, and the predetermined period of the accumulated period is 18 minutes.

7. The cerebral-ischemia supervisory monitor according to claim 4, wherein:
   the light-receiving portion separately receives the ultraviolet rays which are reflected from a cerebrum and the fluorescence which is emitted according to the ultraviolet rays; and
   with respect to two reflected-light intensities which are continually calculated, if the reflected-light intensity which is calculated this time is greater than the reflected-light intensity which was calculated the preceding time, then the control portion is configured to not accumulate this period of time, even tough the fluorescence-intensity change rate in fluorescence intensity which is calculated this time is the predetermined value or higher.

* * * * *